(12) United States Patent
Kawakami et al.

(10) Patent No.: US 9,371,341 B2
(45) Date of Patent: Jun. 21, 2016

(54) CYCLIC AMINOORGANOXYSILANE COMPOUND AND ITS PRODUCTION METHOD

(71) Applicant: SHIN-ETSU CHEMICAL CO., LTD., Tokyo (JP)

(72) Inventors: Masato Kawakami, Joetsu (JP); Yoichi Tonomura, Joetsu (JP); Tohru Kubota, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/881,731

(22) Filed: Oct. 13, 2015

(65) Prior Publication Data

US 2016/0102111 A1    Apr. 14, 2016

(30) Foreign Application Priority Data

Oct. 14, 2014    (JP) .................................. 2014-209951

(51) Int. Cl.
*C07F 7/10*    (2006.01)
*C07F 7/18*    (2006.01)

(52) U.S. Cl.
CPC ................ *C07F 7/1892* (2013.01); *C07F 7/10* (2013.01); *C07F 7/1836* (2013.01); *C07F 7/1844* (2013.01)

(58) Field of Classification Search
CPC ............................... C07F 7/10; C07F 7/1836
USPC ................................................ 556/407, 408
See application file for complete search history.

(56) References Cited

U.S. PATENT DOCUMENTS

2005/0080284 A1    4/2005 Kuimelis et al.

FOREIGN PATENT DOCUMENTS

JP    2014-1152 A    1/2014

OTHER PUBLICATIONS

Extended European Search Report for Appl. No. 15188754.4 dated Jan. 4, 2016.

Kovacs, I. et al., "The synthesis, crystal structures and NMR spectroscopic investigation of 3,7,10-trimethylsilatranes and carbasilatranes," Journal of Organometallic Chemistry, 2009, vol. 694, pp. 14-20.

*Primary Examiner* — Elvis O Price

(74) *Attorney, Agent, or Firm* — Birch, Stewart, Kolasch & Birch, LLP

(57) ABSTRACT

A method for producing a cyclic aminoorganoxysilane compound is provided. The method comprises the step of conducting dehydrochlorination coupling of a chloroalkylalkoxysilane compound represented by the formula:

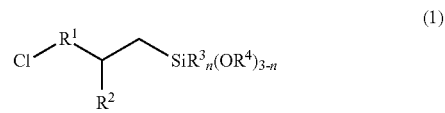

(1)

wherein $R^1$ is a straight or branched divalent $C_{1-10}$ hydrocarbon group, $R^2$ is hydrogen atom or an unsubstituted or substituted $C_{1-10}$ monovalent hydrocarbon group, $R^3$ and $R^4$ are respectively a $C_{1-10}$ monovalent hydrocarbon group, and n is 0, 1, or 2 and an aminoalcohol represented by the formula:

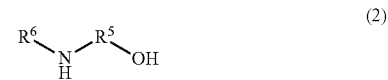

(2)

wherein $R^5$ is a straight or branched $C_{2-10}$ divalent hydrocarbon group which may contain a heteroatom and $R^6$ is hydrogen atom or a straight or branched $C_{1-10}$ monovalent hydrocarbon group, and promoting intramolecular transesterification to thereby produce a cyclic aminoorganoxysilane compound represented by the formula:

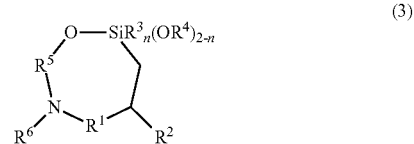

(3)

wherein $R^1$ to $R^6$ and n are as defined above.

3 Claims, 2 Drawing Sheets

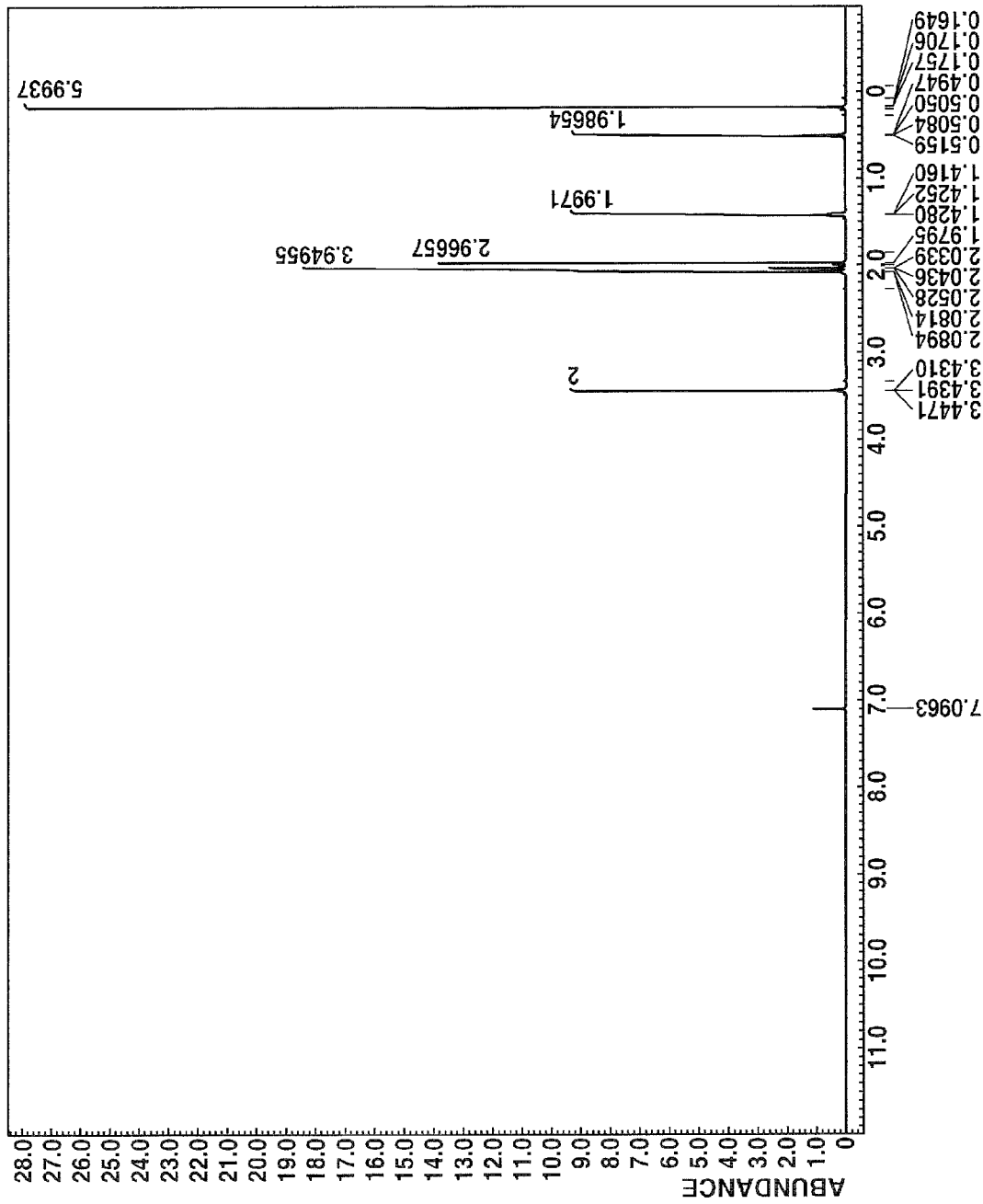

CYCLIC AMINOORGANOXYSILANE COMPOUND AND ITS PRODUCTION METHOD

CROSS-REFERENCE TO RELATED APPLICATION

This non-provisional application claims priority under 35 U.S.C. §119(a) on Patent Application No. 2014-209951 filed in Japan on Oct. 14, 2014, the entire contents of which are hereby incorporated by reference.

TECHNICAL FIELD

The present invention relates to a cyclic aminoorganoxysilane compound which is useful as a silane coupling agent, surface treating agent, resin additive, coating additive, adhesive, and the like. This invention also relates to its production method.

BACKGROUND ART

Aminoorganoxysilane compounds are useful as a silane coupling agent, surface treating agent, resin additive, coating additive, and adhesive, and in particular, the use of a cyclic aminoorganoxysilane compound for such application is quite useful in view of reducing environmental burden since the amount of a low-boiling alcohol component generated is smaller than the conventional aminoorganoxysilane compound. A cyclic aminoorganoxysilane compound is generally produced at a high yield from an epoxy compound and a primary or secondary aminosilane compound by coupling the epoxy compound and the primary or secondary aminosilane compound and thereafter conducting intramolecular transesterification (Patent Document 1: JP-A 2014-1152).

CITATION LIST

Patent Document 1: JP-A 2014-1152

DISCLOSURE OF THE INVENTION

However, the epoxy compound used for the starting material requires a careful handling since it has the risk of undergoing polymerization, and the secondary aminosilane compound is an expensive starting material.

This problem may be solved by changing the starting materials. For example, a cyclic aminoorganoxysilane compound may be produced by alkenylating an aminoalcohol with a chloroalkenyl compound, protecting the free hydroxy group, hydrosilylating the alkenyl group, and finally conducting removal the protecting group and intramolecular transesterification. However, this is a method involving an increased number of steps requiring extensive labor due to the repeated reaction and purification.

The present invention has been completed in view of the situation as described above, and an object of the present invention is to provide a novel cyclic aminoorganoxysilane compound which can be produced by using an inexpensive starting material with handling convenience and which can be produced in short steps. The present invention also provides its production method.

The inventors of the present invention conducted intensive study and found that a cyclic aminoorganoxysilane compound can be produced by an efficient production method, namely, that a novel cyclic aminoorganoxysilane compound represented by the following general formula (1) can be produced merely by 2 production steps and 1 purification step when a chloroalkylalkoxysilane compound and an aminoalcohol are connected by dehydrochlorination coupling reaction, and intramolecular transesterification is conducted after optional removal of the aminoalcohol hydrochloride byproduct. The present invention has been completed on the basis of such findings.

Accordingly, the present invention provides the cyclic aminoorganoxysilane compound produced by using a chloroalkylalkoxysilane compound and an aminoalcohol for the starting materials as described below. The present invention also provides its production method as described below.

[1] A method for producing a cyclic aminoorganoxysilane compound comprising the step of conducting dehydrochlorination coupling of a chloroalkylalkoxysilane compound represented by the following general formula (1):

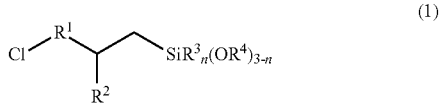

(1)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are respectively a monovalent hydrocarbon group containing 1 to 10 carbon atoms, and n is 0, 1, or 2 and an aminoalcohol represented by the following general formula (2):

(2)

wherein $R^5$ is a straight or branched divalent hydrocarbon group containing 2 to 10 carbon atoms which may contain a heteroatom and $R^6$ is hydrogen atom or a straight or branched monovalent hydrocarbon group containing 1 to 10 carbon atoms, and promoting intramolecular transesterification to thereby produce a cyclic aminoorganoxysilane compound represented by the following general formula (3):

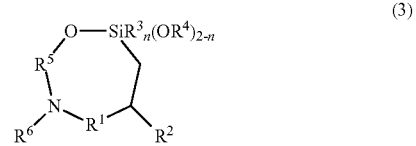

(3)

wherein $R^1$ to $R^6$ and n are as defined above.

[2] The method for producing the cyclic aminoorganoxysilane compound represented by the general formula (3) of [1] comprising the steps of conducting dehydrochlorination coupling of the chloroalkylalkoxysilane compound represented by the general formula (1) and the aminoalcohol represented by the general formula (2), separating and removing hydrochloric salt of the aminoalcohol represented by the general formula (2) by a separation procedure, and promoting intramolecular transesterification.

[3] A cyclic aminoorganoxysilane compound represented by the following general formula (4):

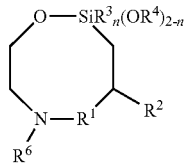
(4)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are a monovalent hydrocarbon group containing 1 to 10 carbon atoms, $R^6$ is hydrogen atom or a straight or branched monovalent hydrocarbon group containing 1 to 10 carbon atoms, and n is 0, 1, or 2.

Advantageous Effects of the Invention

The cyclic aminoorganoxysilane compound provided by the present invention has reduced environmental burden due to the reduced amount of the low boiling alcohol component generated in the use of the compound for the coating additive, adhesive, silane coupling agent, fiber treating agent, and surface treating agent. In addition, the cyclic aminoorganoxysilane compound is efficiently produced from cheaper starting materials with fewer steps compared to other methods.

BRIEF DESCRIPTION OF THE DRAWINGS

FIG. 2 is a $^1$H-NMR spectrum of the 1-oxa-4,8,8-trimethyl-4-aza-8-silacyclooctane obtained in Example 1.

DESCRIPTION OF THE PREFERRED EMBODIMENTS

Figure 1:
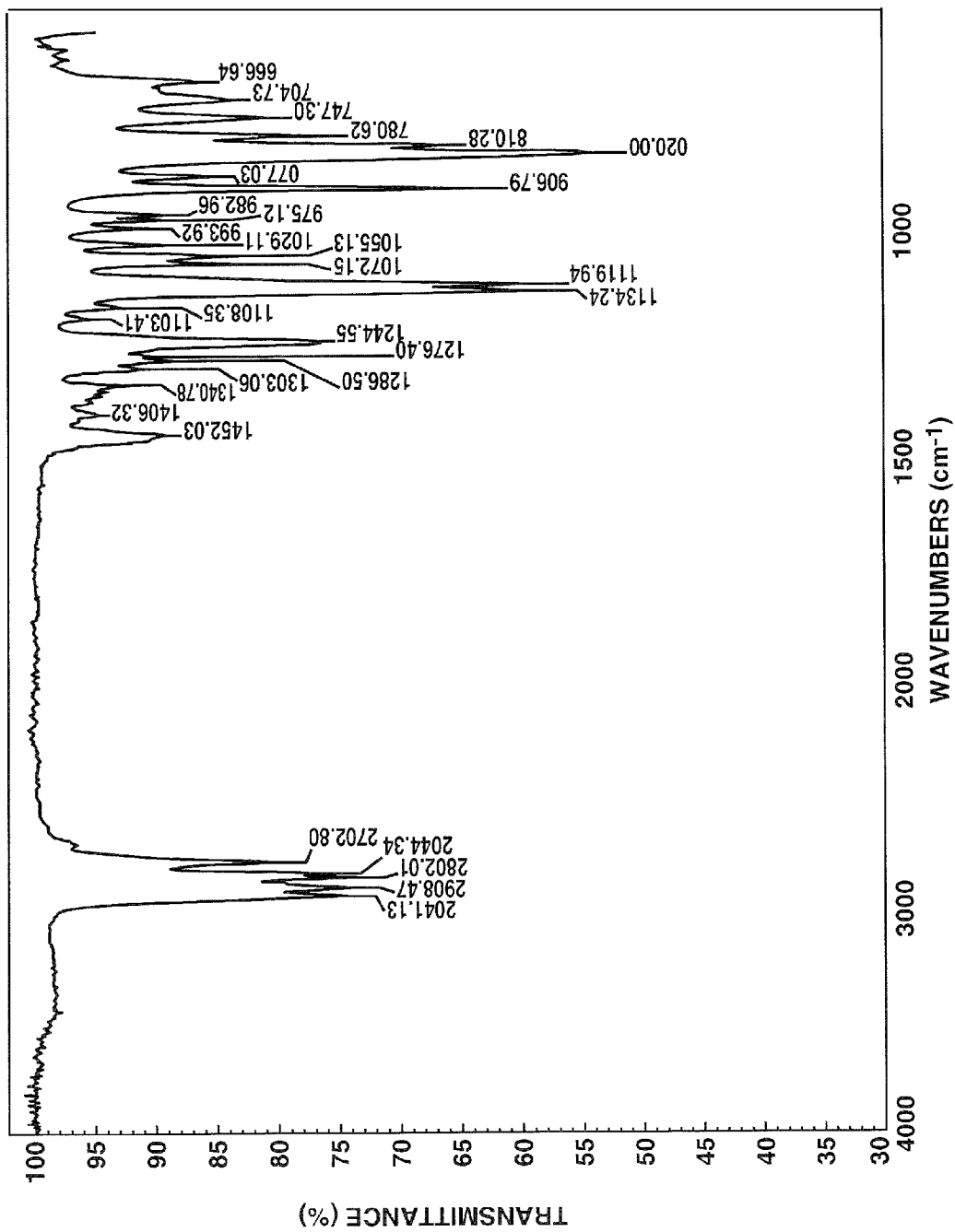
FIG. 1 is an IR spectrum of the 1-oxa-4,8,8-trimethyl-4-aza-8-silacyclooctane obtained in Example 1.

The method for producing a cyclic aminoorganoxysilane compound provided by the present invention is typically a method comprising the step of conducting dehydrochlorination coupling of a chloroalkylalkoxysilane compound represented by the following general formula (1):

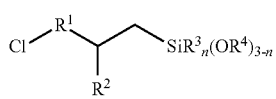
(1)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are respectively a monovalent hydrocarbon group containing 1 to 10 carbon atoms, and n is 0, 1, or 2 and an aminoalcohol represented by the following general formula (2):

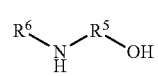
(2)

wherein $R^5$ is a straight or branched divalent hydrocarbon group containing 2 to 10 carbon atoms which may contain a heteroatom and $R^6$ is hydrogen atom or a straight or branched monovalent hydrocarbon group containing 1 to 10 carbon atoms, and promoting intramolecular transesterification to thereby produce a cyclic aminoorganoxysilane compound.

$R^1$ is a divalent hydrocarbon group, and more specifically, a straight or branched divalent hydrocarbon group containing 1 to 10, and preferably 1 to 6 carbon atoms, and examples include alkylene groups such as methylene group, ethylene group, trimethylene group, tetramethylene group, hexamethylene ring, and isobutylene group. The most preferred is methylene group in view of the availability of the starting material.

$R^2$ is hydrogen atom or an unsubstituted or substituted monovalent hydrocarbon group containing 1 to 10, and preferably 1 to 6 carbon atoms, and examples include straight chain alkyl groups such as methyl group, ethyl group, propyl group, butyl group, pentyl group, hexyl group, heptyl group, octyl group, and decyl group, branched alkyl groups such as isopropyl group, isobutyl group, and tert-butyl group, cyclic alkyl groups such as cyclopentyl group and cyclohexyl group, alkenyl groups such as vinyl group, allyl group, and propenyl group, aryl groups such as phenyl group and tolyl group, and aralkyl groups such as benzyl group and phenethyl group. The most preferred is hydrogen atom or methyl group in view of the availability of the starting material and the relatively low boiling point of the intended resulting compound. In addition, the hydrocarbon group may have some or all of their hydrogen atoms respectively substituted with a substituent, and exemplary substituents include alkoxy groups such as methoxy group, ethoxy group, and (iso)propoxy group; groups comprising a halogen atom such as fluorine atom, chlorine atom, bromine atom, or iodine atom, cyano group, amino group, ester group, alkyl group having an intervening ether oxygen, acyl group, sulfide group, alkyl silyl group, and alkoxysilyl group, which may be used in combination of two or more.

Examples of the compound of the formula (1) having an alkyl group having an intervening ether oxygen are as shown below.

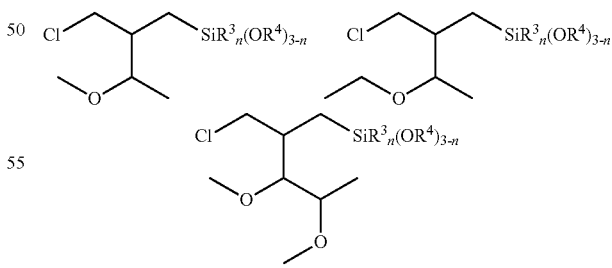

wherein $R^3$, $R^4$, and n are as defined above.

$R^3$ and $R^4$ are respectively a monovalent hydrocarbon group containing 1 to 10, and preferably 1 to 6 carbon atoms, and exemplary such groups include straight chain alkyl groups such as methyl group, ethyl group, propyl group, butyl group, pentyl group, hexyl group, heptyl group, octyl group, and decyl group, branched alkyl groups such as isopropyl group, isobutyl group, and tert-butyl group, cyclic alkyl groups such as cyclopentyl group and cyclohexyl group, alkenyl groups such as vinyl group, allyl group, and propenyl group, aryl groups such as phenyl group and tolyl group, and aralkyl groups such as benzyl group and phenethyl group. The preferred are methyl group and ethyl group in view of the high utility of the resulting product.

$R^5$ is a divalent hydrocarbon group containing 2 to 10, and preferably 2 to 6 carbon atoms which may optionally contain a heteroatom. Exemplary such groups include straight chain alkylene groups such as methylene group, ethylene group, trimethylene group, tetramethylene group, and hexamethylene group and branched alkylene groups such as isobutylene group. The most preferred is methylene group in view of the availability of the starting material.

$R^6$ is hydrogen atom or an unsubstituted or substituted monovalent hydrocarbon group containing 1 to 10, and preferably 1 to 6 carbon atoms, and exemplary such groups include straight chain alkyl groups such as methyl group, ethyl group, propyl group, butyl group, pentyl group, hexyl group, heptyl group, octyl group, and decyl group, branched alkyl groups such as isopropyl group, isobutyl group, and tert-butyl group, cyclic alkyl groups such as cyclopentyl group and cyclohexyl group, alkenyl groups such as vinyl group, allyl group, and propenyl group, aryl groups such as phenyl group and tolyl group, and aralkyl groups such as benzyl group and phenethyl group. In view of the availability of the starting material and the high utility of the intended resulting compound, the preferred are hydrogen atom, methyl group, ethyl group, or phenyl group.

Exemplary chloroalkylalkoxysilane compounds represented by the general formula (1) include chloropropyldimethylmethoxysilane, chloropropylmethyldimethoxysilane, chloropropyltrimethoxysilane, chloropropyldimethylethoxysilane, chloropropylmethyldiethoxysilane, chloropropyltriethoxysilane, 3-chloro-2-methylpropyldimethylmethoxysilane, 3-chloro-2-methylpropylmethyldimethoxysilane, 3-chloro-2-methylpropyltrimethoxysilane, 3-chloro-2-methylpropyldimethylethoxysilane, 3-chloro-2-methylpropylmethyldiethoxysilane, 3-chloro-2-methylpropyltriethoxysilane, chlorobutyldimethylmethoxysilane, chlorobutylmethyldimethoxysilane, chlorobutyltrimethoxysilane, chlorobutyldimethylethoxysilane, chlorobutylmethyldiethoxysilane, chlorobutyltriethoxysilane, 4-chloro-2-methylbutyldimethylmethoxysilane, 4-chloro-2-methylbutylmethyldimethoxysilane, 4-chloro-2-methylbutyltrimethoxysilane, 4-chloro-2-methylbutyldimethylethoxysilane, 4-chloro-2-methylbutylmethyldiethoxysilane, 4-chloro-2-methylbutyltriethoxysilane, chloropentyldimethylmethoxysilane, chloropentylmethyldimethoxysilane, chloropentyltrimethoxysilane, chloropentyldimethylethoxysilane, chloropentylmethyldiethoxysilane, chloropentyltriethoxysilane, 5-chloro-2-methylpentyldimethylmethoxysilane, 5-chloro-2-methylpentylmethyldimethoxysilane, 5-chloro-2-methylpentyltrimethoxysilane, 5-chloro-2-methylpentyldimethylethoxysilane, 5-chloro-2-methylpentylmethyldiethoxysilane, 5-chloro-2-methylpentyltriethoxysilane, chlorohexyldimethylmethoxysilane, chlorohexylmethyldimethoxysilane, chlorohexyltrimethoxysilane, chlorohexyldimethylethoxysilane, chlorohexylmethyldiethoxysilane, chlorohexyltriethoxysilane, 6-chloro-2-methylhexyldimethylmethoxysilane, 6-chloro-2-methylhexylmethyldimethoxysilane, 6-chloro-2-methylhexyltrimethoxysilane, 6-chloro-2-methylhexyldimethylethoxysilane, 6-chloro-2-methylhexylmethyldiethoxysilane, and 6-chloro-2-methylhexyltriethoxysilane.

Exemplary aminoalcohols represented by the general formula (2) include aminoethanol, methylaminoethanol, ethylaminoethanol, aminopropanol, methylaminopropanol, ethylaminopropanol, aminobutanol, methylaminobutanol, ethylaminobutanol, aminoisopropanol, methylaminoisopropanol, aminoethoxyethanol, methylaminoethoxyethanol, ethylaminoethoxyethanol, and anilinoethanol.

The blend ratio of the chloroalkylalkoxysilane compound represented by the general formula (1) and the aminoalcohol represented by the general formula (2) is not particularly limited. The blend ratio, however, is preferably in the range of 0.1 to 4 moles, and in particular, 0.2 to 3 moles of the aminoalcohol represented by the general formula (2) in relation to 1 mole of the compound represented by the general formula (1) in view of the reactivity and the productivity.

The reaction temperature in the dehydrochlorination coupling reaction is not particularly limited. This reaction, however, is preferably conducted at 50 to 200° C., and in particular, at 100 to 150° C. The reaction time is also not particularly limited while the preferable reaction time is 1 to 40 hours, and in particular, 1 to 20 hours.

The dehydrochlorination coupling reaction may proceed either in the absence of a solvent or by using a solvent. Exemplary solvents used include hydrocarbon solvents such as pentane, hexane, cyclohexane, heptane, isooctane, benzene, toluene, and xylene, alcohol solvents such as methanol, ethanol, and isopropanol, ether solvents such as diethylether, tetrahydrofuran, and dioxane, and aprotic polar solvents such as acetonitrile, N,N-dimethylformamide, and N-methylpyrrolidone, which may be used alone or as a mixture of two or more. Use of an alcohol solvent is preferable in view of preventing the polymerization of the compound.

The catalyst used in the induction to the general formula (3) by the intramolecular transesterification may be the catalyst commonly used in the transesterification. Exemplary such transesterification catalysts include sodium methoxide, sodium ethoxide, and the like as well as their alcohol solution; basic catalysts such as potassium methoxide, potassium ethoxide, sodium hydroxide, potassium hydroxide, cesium hydroxide, calcium hydroxide, and magnesium hydroxide; acidic catalysts such as hydrogen chloride, hydrogen bromide, sulfuric acid, benzene sulfonic acid, dodecylbenzenesulfonic acid, trifluoromethanesulfonic acid, acetic acid, and trifluoroacetic acid; and quarternary ammonium hydroxides such as tetramethylammonium hydroxide, tetraethylammonium hydroxide, tetrapropylammonium hydroxide, tetrabutylammonium hydroxide, and trimethylbenzylammonium hydroxide.

The amount of the catalyst used is not particularly limited. The catalyst, however, is preferably used at an amount in the range of 0.001 to 1.0 mole, more preferably 0.001 to 0.2 mole, and most preferably 0.005 to 0.1 mole in relation to 1 mole of the compound represented by the general formula (1). When the amount of the catalyst is less than 0.001 mole, sufficient effect of the catalyst addition may not be realized. When the amount of the catalyst is in excess of 1.0 mole, the reaction promotion effect may not be increased any more.

The reaction temperature in the intramolecular transesterification is not particularly limited while the preferred is the reaction at 60 to 200° C., and in particular, 100 to 150° C. The reaction time is also not particularly limited while the preferable reaction time is 3 to 30 hours, and in particular 6 to 15 hours. The reaction is preferably conducted in the atmosphere of an inert gas such as nitrogen or argon.

While the intramolecular transesterification proceeds in the absence of the solvent, the reaction may be efficiently promoted by conducting the reaction by refluxing the solvent and distilling off the resulting alcohol with the solvent. Examples of the solvent used include hydrocarbon solvents such as pentane, hexane, cyclohexane, heptane, isooctane, decane, dodecane, tridecane, tetradecane, hexadecane, benzene, toluene, and xylene, ether solvents such as diethylether, tetrahydrofuran, and dioxane, aprotic polar solvents such as acetonitrile, N,N-dimethylformamide, and N-methylpyrrolidone.

The cyclic aminoorganoxysilane compound provided by the present invention is the compound represented by the following general formula (3):

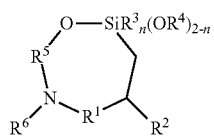

(3)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are respectively a monovalent hydrocarbon group containing 1 to 10 carbon atoms, $R^5$ is a straight or branched divalent hydrocarbon group containing 2 to 10 carbon atoms which may contain a heteroatom, $R^6$ is hydrogen atom or a straight or branched monovalent hydrocarbon group containing 1 to 10 carbon atoms, and n is 0, 1, or 2.

Exemplary cyclic aminoorganoxysilane compounds represented by the general formula (3) include
2-methyl-8,8-dimethoxy-1-oxa-4-aza-8-silacyclooctane,
2,8-dimethyl-8-methoxy-1-oxa-4-aza-8-silacyclooctane,
2-methyl-8,8-diethoxy-1-oxa-4-aza-8-silacyclooctane,
2,8-dimethyl-8-ethoxy-1-oxa-4-aza-8-silacyclooctane,
1-oxa-2,8,8-trimethyl-4-aza-8-silacyclooctane,
2-ethyl-8,8-dimethoxy-1-oxa-4-aza-8-silacyclooctane,
2-ethyl-8-methoxy-8-methyl-1-oxa-4-aza-8-silacyclooctane,
2-ethyl-8,8-diethoxy-1-oxa-4-aza-8-silacyclooctane,
8-ethoxy-2-ethyl-8-methyl-1-oxa-4-aza-8-silacyclooctane,
8,8-dimethyl-2-ethyl-1-oxa-4-aza-8-silacyclooctane,
2-butyl-8,8-dimethoxy-1-oxa-4-aza-8-silacyclooctane,
2-butyl-8-methoxy-8-methyl-1-oxa-4-aza-8-silacyclooctane,
2-butyl-8,8-diethoxy-1-oxa-4-aza-8-silacyclooctane,
2-butyl-8-ethoxy-8-methyl-1-oxa-4-aza-8-silacyclooctane,
2-butyl-8,8-dimethyl-1-oxa-4-aza-8-silacyclooctane,
2-allyl-8,8-dimethoxy-1-oxa-4-aza-8-silacyclooctane,
2-allyl-8-methoxy-8-methyl-1-oxa-4-aza-8-silacyclooctane,
2-allyl-8,8-diethoxy-1-oxa-4-aza-8-silacyclooctane,
2-allyl-8-ethoxy-8-methyl-1-oxa-4-aza-8-silacyclooctane,
2-allyl-8,8-dimethyl-1-oxa-4-aza-8-silacyclooctane,
2-(5,5,5,4,4,3,3,2,2-nonafluoropentyl)-8,8-dimethoxy-4-methyl-1-oxa-4-aza-8-silacyclooctane,
2-(5,5,5,4,4,3,3,2,2-nonafluoropentyl)-4,8-dimethyl-8-methoxy-1-oxa-4-aza-8-silacyclooctane,
2-(5,5,5,4,4,3,3,2,2-nonafluoropentyl)-8,8-diethoxy-4-methyl-1-oxa-4-aza-8-silacyclooctane,
2-(5,5,5,4,4,3,3,2,2-nonafluoropentyl)-4,8-dimethyl-8-ethoxy-1-oxa-4-aza-8-silacyclooctane, and
2-(5,5,5,4,4,3,3,2,2-nonafluoropentyl)-1-oxa-4,8,8-trimethyl-4-aza-8-silacyclooctane.

The cyclic aminoorganoxysilane compounds represented by the general formula (3) include the compound represented by the following general formula (4):

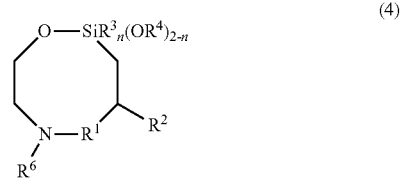

(4)

wherein $R^1$ to $R^4$, $R^6$, and n are as defined above.

Exemplary compounds represented by the general formula (4) include 8,8-dimethyl-1-oxa-4-aza-8-silacyclooctane, 8-methoxy-8-methyl-1-oxa-4-aza-8-silacyclooctane, 8,8-dimethoxy-1-oxa-4-aza-8-silacyclooctane, 8-ethoxy-8-methyl-1-oxa-4-aza-8-silacyclooctane, 8,8-diethoxy-1-oxa-4-aza-8-silacyclooctane, 1-oxa-4,8,8-trimethyl-4-aza-8-silacyclooctane, 4,8-dimethyl-8-methoxy-1-oxa-4-aza-8-silacyclooctane, 8,8-dimethoxy-4-methyl-1-oxa-4-aza-8-silacyclooctane, 4,8-dimethyl-8-ethoxy-1-oxa-4-aza-8-silacyclooctane, 8,8-diethoxy-4-methyl-1-oxa-4-aza-8-silacyclooctane, 8,8-dimethyl-4-ethyl-1-oxa-4-aza-8-silacyclooctane, 4-ethyl-8-methoxy-8-methyl-1-oxa-4-aza-8-silacyclooctane, 8,8-dimethoxy-4-ethyl-1-oxa-4-aza-8-silacyclooctane, 8-ethoxy-4-ethyl-8-methyl-1-oxa-4-aza-8-silacyclooctane, 8,8-diethoxy-4-ethyl-1-oxa-4-aza-8-silacyclooctane, 8,8-dimethyl-1-oxa-4-phenyl-4-aza-8-silacyclooctane, 8-methoxy-8-methyl-1-oxa-4-phenyl-4-aza-8-silacyclooctane, 8,8-dimethoxy-1-oxa-4-phenyl-4-aza-8-silacyclooctane, 8-ethoxy-8-methyl-1-oxa-4-phenyl-4-aza-8-silacyclooctane, 8,8-diethoxy-1-oxa-4-phenyl-4-aza-8-silacyclooctane, 1-oxa-6,8,8-trimethyl-4-aza-8-silacyclooctane, 6,8-dimethyl-8-methoxy-1-oxa-4-aza-8-silacyclooctane, 8,8-dimethoxy-6-methyl-1-oxa-4-aza-8-silacyclooctane, 6,8-dimethyl-8-ethoxy-1-oxa-4-aza-8-silacyclooctane, 8,8-diethoxy-6-methyl-1-oxa-4-aza-8-silacyclooctane, 1-oxa-4,6,8,8-tetramethyl-4-aza-8-silacyclooctane, 8-methoxy-1-oxa-4,6,8-trimethyl-4-aza-8-silacyclooctane, 8,8-dimethoxy-4,6-dimethyl-1-oxa-4-aza-8-silacyclooctane, 8-ethoxy-1-oxa-4,6,8-trimethyl-4-aza-8-silacyclooctane, 8,8-diethoxy-4,6-dimethyl-1-oxa-4-aza-8-silacyclooctane, 4-ethyl-1-oxa-6,8,8-trimethyl-4-aza-8-silacyclooctane, 6,8-dimethyl-4-ethyl-8-methoxy-1-oxa-4-aza-8-silacyclooctane, 8,8-dimethoxy-4-ethyl-6-methyl-1-oxa-4-aza-8-silacyclooctane, 6,8-dimethyl-4-ethyl-8-ethoxy-1-oxa-4-aza-8-silacyclooctane, 8,8-diethoxy-4-ethyl-6-methyl-1-oxa-4-aza-8-silacyclooctane, 1-oxa-4-phenyl-6,8,8-trimethyl-4-aza-8-silacyclooctane, 6,8-dimethyl-8-methoxy-1-oxa-4-phenyl-4-aza-8-silacyclooctane, 8,8-dimethoxy-6-methyl-1-oxa-4-phenyl-4-aza-8-silacyclooctane, 6,8-dimethyl-8-ethoxy-1-oxa-4-phenyl-4-aza-8-silacyclooctane, 8,8-diethoxy-6-methyl-1-oxa-4-phenyl-4-aza-8-silacyclooctane, 9,9-dimethyl-1-oxa-4-aza-9-silacyclononane, 9-methoxy-9-methyl-1-oxa-4-aza-9-silacyclononane, 9,9-dimethoxy-1-oxa-4-aza-9-silacyclononane, 9-ethoxy-9-methyl-1-oxa-4-aza-9-silacyclononane, 9,9-diethoxy-1-oxa-4-aza-9-silacyclononane, 1-oxa-4,9,9-trimethyl-4-aza-9-silacyclononane, 4,9-dimethyl-9-methoxy-1-oxa-4-aza-9-silacyclononane, 9,9-dimethoxy-4-methyl-1-oxa-4-aza-9-silacyclononane, 4,9-dimethyl-9-ethoxy-1-oxa-4-aza-9-silacyclononane, 9,9-diethoxy-4-methyl-1-oxa-4-aza-9-silacyclononane, 9,9-dimethyl-4-ethyl-1-oxa-4-aza-9- silacyclononane, 4-ethyl-9-methoxy-9-methyl-1-oxa-4-aza-9-silacyclononane, 9,9-dimethoxy-4-ethyl-1-oxa-4-aza-9-silacyclononane, 9-ethoxy-4-ethyl-9-methyl-1-oxa-4-aza-9-silacyclononane, 9,9-diethoxy-4-ethyl-1-oxa-4-aza-9-silacyclononane, 9,9-dimethyl-1-oxa-4-phenyl-4-aza-9-silacyclononane, 9-methoxy-9-methyl-1-oxa-4-phenyl-4-aza-9-silacyclononane, 9,9-dimethoxy-1-oxa-4-phenyl-4-aza-9-silacyclononane, 9-ethoxy-9-methyl-1-oxa-4-phenyl-4-aza-9-silacyclononane, 9,9-diethoxy-1-oxa-4-phenyl-4-aza-9-silacyclononane, 10,10-dimethyl-1-oxa-4-aza-10-silacyclodecane, 10-methoxy-10-methyl-1-oxa-4-aza-10-silacyclodecane, 10,10-dimethoxy-1-oxa-4-aza-10-silacyclodecane, 10-ethoxy-10-methyl-1-oxa-4-aza-10-silacyclodecane, 10,10-diethoxy-1-oxa-4-aza-10-silacyclodecane, 1-oxa-4,10,10-trimethyl-4-aza-10-silacyclodecane, 4,10-dimethyl-10-methoxy-1-oxa-4-aza-10-silacyclodecane, 10,10-dimethoxy-4-methyl-1-oxa-4-aza-10-silacyclodecane, 4,10-dimethyl-10-ethoxy-1-oxa-4-aza-10-silacyclodecane, 10,10-diethoxy-4-methyl-1-oxa-4-aza-10-silacyclodecane, 10,10-dimethyl-4-ethyl-1-oxa-4-aza-10-silacyclodecane, 4-ethyl-10-methoxy-10-methyl-1-oxa-4-aza-10-silacyclodecane, 10,10-dimethoxy-4-ethyl-1-oxa-4-aza-10-silacyclodecane, 10-ethoxy-4-ethyl-10-methyl-1-oxa-4-aza-10-silacyclodecane, 10,10-diethoxy-4-ethyl-1-oxa-4-aza-10-silacyclodecane, 10,10-dimethyl-1-oxa-4-phenyl-4-aza-10-silacyclodecane, 10-methoxy-10-methyl-1-oxa-4-phenyl-4-aza-10-silacyclodecane, 10,10-dimethoxy-1-oxa-4-phenyl-4-aza-10-silacyclodecane, 10-ethoxy-10-methyl-1-oxa-4-phenyl-4-aza-10-silacyclodecane, 10,10-diethoxy-1-oxa-4-phenyl-4-aza-10-silacyclodecane, 11,11-dimethyl-1-oxa-4-aza-11-silacycloundecane, 11-methoxy-11-methyl-1-oxa-4-aza-11-silacycloundecane, 11,11-dimethoxy-1-oxa-4-aza-11-silacycloundecane, 11-ethoxy-11-methyl-1-oxa-4-aza-11-silacycloundecane, 11,11-diethoxy-1-oxa-4-aza-11-silacycloundecane, 1-oxa-4,11,11-trimethyl-4-aza-11-silacycloundecane, 4,11-dimethyl-11-methoxy-1-oxa-4-aza-11-silacycloundecane, 11,11-dimethoxy-4-methyl-1-oxa-4-aza-11-silacycloundecane, 4,11-dimethyl-11-ethoxy-1-oxa-4-aza-11-silacycloundecane, 11,11-diethoxy-4-methyl-1-oxa-4-aza-11-silacycloundecane, 11,11-dimethyl-4-ethyl-1-oxa-4-aza-11-silacycloundecane, 4-ethyl-11-methoxy-11-methyl-1-oxa-4-aza-11-silacycloundecane, 11,11-dimethoxy-4-ethyl-1-oxa-4-aza-11-silacycloundecane, 11-ethoxy-4-ethyl-11-methyl-1-oxa-4-aza-11-silacycloundecane, 11,11-diethoxy-4-ethyl-1-oxa-4-aza-11-silacycloundecane, 11,11-dimethyl-1-oxa-4-phenyl-4-aza-11-silacycloundecane, 11-methoxy-11-methyl-1-oxa-4-phenyl-4-aza-11-silacycloundecane, 11,11-dimethoxy-1-oxa-4-phenyl-4-aza-11-silacycloundecane, 11-ethoxy-11-methyl-1-oxa-4-phenyl-4-aza-11-silacycloundecane, 11,11-diethoxy-1-oxa-4-phenyl-4-aza-11-silacycloundecane, 11,11-dimethyl-1,4-dioxa-7-aza-11-silacycloundecane, 1,4-dioxa-7,11,11-trimethyl-7-aza-11-silacycloundecane, 7,11-dimethyl-1,4-dioxa-11-methoxy-7-aza-11-silacycloundecane, and 11,11-dimethoxy-1,4-dioxa-7-methyl-7-aza-11-silacycloundecane.

EXAMPLES

Next, the present invention is described in further detail by referring to the Examples which by no means limit the scope of the present invention.

Example 1

Synthesis of 1-oxa-4,8,8-trimethyl-4-aza-8-silacyclooctane using Chloropropyldimethylethoxysilane and Methylethanolamine In a flask equipped with a stirrer, a reflux condenser, a dropping funnel, and a thermometer, 180.9 g (1.001 mole) of chloropropyldimethylethoxysilane and 38.2 g of ethanol were charged, and the mixture was refluxed. After stabilization of the inner temperature to 85° C., 157.7 g (2.100 moles) of methylethanolamine was added dropwise in 3 hours, and the stirring was continued for 14 hours under reflux. After cooling the reaction mixture to room temperature, 126.4 g of toluene was added to the reaction mixture, and methylethanolamine hydrochloride was removed by using a separatory funnel to obtain the cyclized precursor reaction mixture.

In a flask equipped with a stirrer, a reflux condenser, a dropping funnel, and a thermometer, 606.2 g of toluene and 6.5 g (0.020 mole) of dodecylbenzenesulfonic acid were charged, and the mixture was refluxed. After stabilization of the inner temperature to 110° C., the cyclized precursor reaction mixture was added dropwise in 12 hours and the solvent was simultaneously extracted. After the completion of the dropwise addition, the solvent was further extracted for 2 hours to obtain the reaction mixture. The resulting reaction mixture was distilled to obtain 126.2 g of a fraction having a boiling point of 67° C./2.0 kPa.

The thus obtained fraction was evaluated by mass spectrum, $^1$H-NMR spectrum, and IR spectrum.

Mass spectrum: m/z 173, 158, 130, 116, 89, 75

$^1$H-NMR spectrum (solvent, deuterobenzene): shown in the chart of FIG. 1.

IR spectrum: shown in the chart of FIG. 2.

These results confirmed that the resulting compound was 1-oxa-4,8-8-trimethyl-4-aza-8-silacyclooctane.

Example 2

Synthesis of 1-oxa-4,8,8-trimethyl-4-aza-8-silacyclooctane using Chloropropyldimethylmethoxysilane and Methylethanolamine In a flask equipped with a stirrer, a reflux condenser, a dropping funnel, and a thermometer, 166.7 g (1.001 mole) of chloropropyldimethylmethoxysilane and 37.5 g of methanol were charged, and the mixture was refluxed. After stabilization of the inner temperature to 70° C., 157.7 g (2.100 mole) of methylethanolamine was added dropwise in 3 hours, and the stirring was continued for 14 hours under reflux. After cooling the reaction mixture to room temperature, 127.7 g of toluene was added to the reaction mixture, and methylethanolamine hydrochloride was removed by using a separatory funnel to obtain the cyclized precursor reaction mixture.

In a flask equipped with a stirrer, a reflux condenser, a dropping funnel, and a thermometer, 613.8 g of toluene and 6.5 g (0.020 mole) of dodecylbenzenesulfonic acid were charged, and the mixture was refluxed. After stabilization of the inner temperature to 110° C., the cyclized precursor reaction mixture was added dropwise in 12 hours and the solvent was simultaneously extracted. After the completion of the dropwise addition, the solvent was further extracted for 2 hours to obtain the reaction mixture. The resulting reaction mixture was distilled to obtain 105.8 g of a fraction having a boiling point of 67° C./2.0 kPa.

Japanese Patent Application No. 2014-209951 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for producing a cyclic aminoorganoxysilane compound comprising the step of conducting dehydrochlorination coupling of a chloroalkylalkoxysilane compound represented by the following general formula (1):

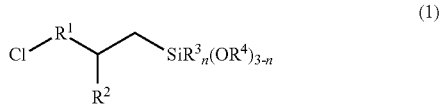
(1)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are respectively a monovalent hydrocarbon group containing 1 to 10 carbon atoms, and n is 0, 1, or 2 and an aminoalcohol represented by the following general formula (2):

(2)

wherein $R^5$ is a straight or branched divalent hydrocarbon group containing 2 to 10 carbon atoms which may contain a heteroatom and $R^6$ is hydrogen atom or a straight or branched monovalent hydrocarbon group containing 1 to 10 carbon atoms, and promoting intramolecular transesterification to thereby produce a cyclic aminoorganoxysilane compound represented by the following general formula (3):

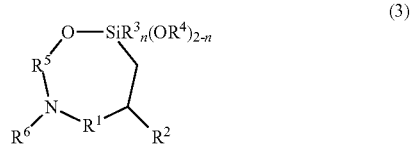
(3)

wherein $R^1$ to $R^6$ and n are as defined above.

2. The method for producing the cyclic aminoorganoxysilane compound represented by the general formula (3) of claim 1 comprising the steps of conducting dehydrochlorination coupling of the chloroalkylalkoxysilane compound represented by the general formula (1) and the aminoalcohol represented by the general formula (2), separating and removing hydrochloric salt of the aminoalcohol represented by the general formula (2) by a separation procedure, and promoting intramolecular transesterification.

3. A cyclic aminoorganoxysilane compound represented by the following general formula (4):

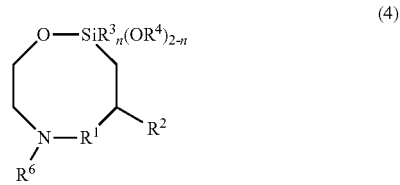
(4)

wherein $R^1$ is a straight or branched divalent hydrocarbon group containing 1 to 10 carbon atoms, $R^2$ is hydrogen atom or an unsubstituted or substituted monovalent hydrocarbon group containing 1 to 10 carbon atoms, $R^3$ and $R^4$ are a monovalent hydrocarbon group containing 1 to 10 carbon atoms, $R^6$ is hydrogen atom or a straight or branched monovalent hydrocarbon group containing 1 to 10 carbon atoms, and n is 0, 1, or 2.

* * * * *